(12) United States Patent
Wadman (10) Patent No.: US 7,649,628 B2
(45) Date of Patent: Jan. 19, 2010

(54) OPTICAL INSPECTION OF TEST SURFACES

(75) Inventor: Sipke Wadman, Waalre (NL)

(73) Assignee: Koninklijke Philips Electronics N.V., Eindhoven (NL)

(*) Notice: Subject to any disclaimer, the term of this patent is extended or adjusted under 35 U.S.C. 154(b) by 465 days.

(21) Appl. No.: 11/576,470

(22) PCT Filed: Oct. 5, 2005

(86) PCT No.: PCT/IB2005/053277

§ 371 (c)(1),
(2), (4) Date: Apr. 2, 2007

(87) PCT Pub. No.: WO2006/038196

PCT Pub. Date: Apr. 13, 2006

(65) Prior Publication Data

US 2009/0116023 A1   May 7, 2009

Related U.S. Application Data

(60) Provisional application No. 60/617,190, filed on Oct. 8, 2004.

(51) Int. Cl.
*G01N 21/55* (2006.01)
(52) U.S. Cl. .................................. 356/445
(58) Field of Classification Search ......... 356/445–448, 356/600–640
See application file for complete search history.

(56) References Cited

U.S. PATENT DOCUMENTS

| | | | | |
|---|---|---|---|---|
| 4,555,635 A * | 11/1985 | Yoshida | .............. | 250/559.46 |
| 4,575,252 A * | 3/1986 | Akiyama | .............. | 356/446 |
| 5,241,369 A * | 8/1993 | McNeil et al. | .............. | 356/445 |
| 5,637,873 A * | 6/1997 | Davis et al. | .............. | 250/339.11 |
| 5,912,741 A * | 6/1999 | Carter et al. | .............. | 356/445 |
| 6,577,397 B1 | 6/2003 | Wadman | | |
| 6,593,925 B1 | 7/2003 | Hakura | | |
| 6,639,685 B1 | 10/2003 | Gu et al. | | |
| 6,697,062 B1 | 2/2004 | Cabral et al. | | |
| 2003/0007159 A1 | 1/2003 | Franke et al. | | |
| 2003/0179197 A1 | 9/2003 | Sloan et al. | | |
| 2003/0234786 A1 | 12/2003 | Cole et al. | | |

OTHER PUBLICATIONS

Philips, "Parousiameter for Hemispherical Scatterometry and Characterisation of Appearance", Printed Jul. 30, 2004 from www/licensing.philips.

* cited by examiner

*Primary Examiner*—Gregory J Toatley, Jr.
*Assistant Examiner*—Jarreas C. Underwood (57) ABSTRACT

In one aspect, the amount of data needed to store image intensity data obtained from a scatterometer (100) such as a Parousiameter is reduced by varying a resolution with which the intensity data is used in different regions of a grid according to determined variations in the intensity. In another aspect, a scatterometer is provided with an aspherical mirror (170, 900, 1000) for imaging a test sample (180) to correct for distortions introduced by the off center placement of the mirror relative to the test sample. In another aspect, an optical surface inspection apparatus uses an auxiliary lens (1440) between a test surface (1420) and an illuminated patterned grid (1410) to project the patterned grid (1610) on the test surface. A camera (1450) is focused on the grid on the test surface as a real image.

15 Claims, 9 Drawing Sheets

OPTICAL INSPECTION OF TEST SURFACES

CROSS REFERENCE TO RELATED APPLICATION

This application claims the benefit of U.S. Provisional Application Ser. No. 60/617,190 filed Oct. 8, 2004, and International Application Number PCT/IB2005/053277, filed Oct. 5, 2005, which are incorporated herein in whole by reference.

The invention relates generally to optical inspection of test surfaces such as on manufactured goods to assess their quality and uniformity and, more particularly, to a scatterometric technique with increased dynamic range and reduced distortion, and to a further technique with increased measuring range.

Figure 1:
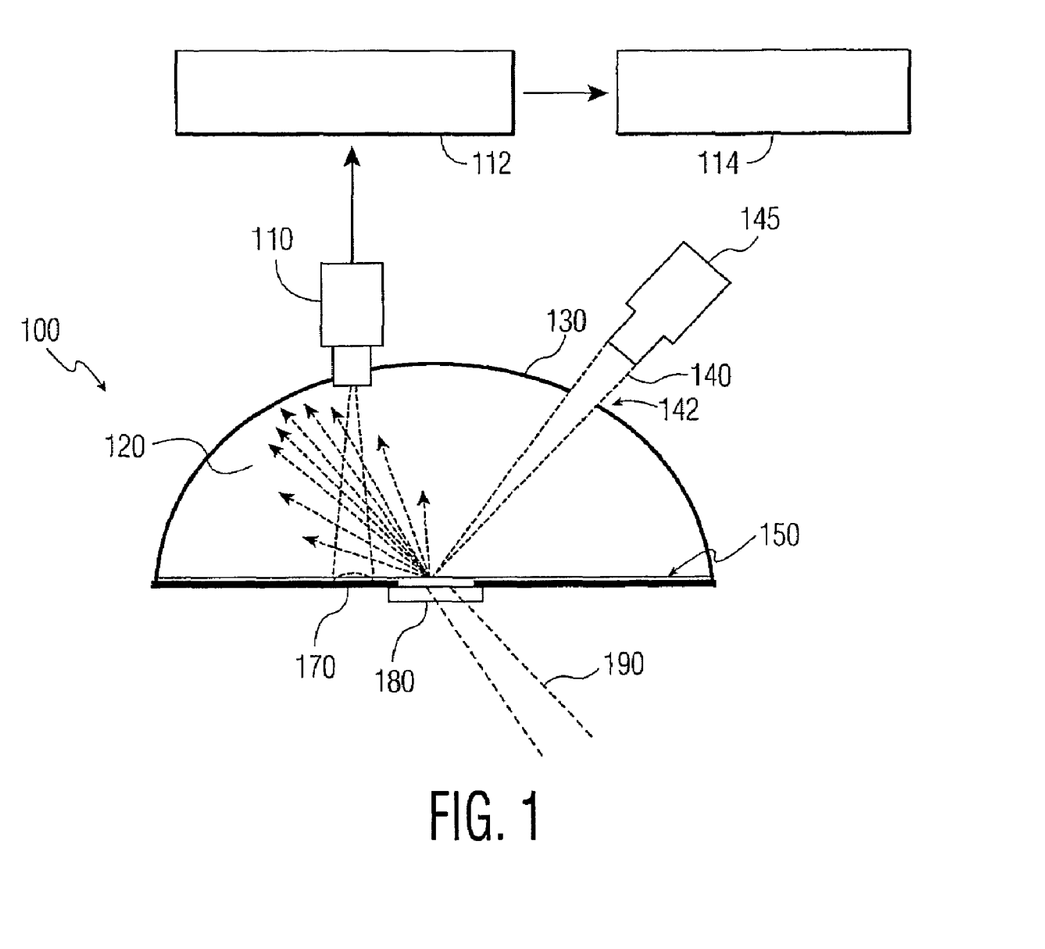
FIG. 1 illustrates a scatterometer for measuring a test sample.

The appearance of products and packaging is important to their appeal to the buyer. For example, it is important to carefully control the color and gloss of a product during the finishing stages of the manufacturing process. Generally, the surface texture of the items affects how light is reflected off the surface and received by the viewer. The scatterometer has been developed as a tool to measure the reflection of light from an object. For example, U.S. Pat. No. 6,577,397 to S. Wadman, incorporated herein by reference, describes a device known as a Parousiameter for performing hemispherical scatterometry. The device illuminates a test surface in an optically controlled way and measures the reflections and/or transmissions in a full hemisphere screen or other portion of a sphere. Such a device allows accurate measurement of brightness and flop effects, e.g., changes in brightness or color that are apparent when the surface is viewed or illuminated from different directions. Referring to FIG. 1, a sample 180 is centrally placed on a surface 150, such as a diffuse black surface, under a reflecting dome or screen 130, which may comprise a diffuse gray surface, and illuminated by a collimated light beam 140 from a light source 145 at one or more angles of incidence. The light beam 140 passes through an aperture 142 in the screen 130. The light 120 scattered off the sample 180 is caught on the hemispherical screen. The screen 130 is imaged in a digital camera 110 such as a CCD camera using wide-angle optics such as a spherical mirror 170. The captured image is then transferred to a computer for analysis by performing data processing 112 (block 112 reads "data processing") and a numerical surface characterization 114 (block 114 reads "numerical surface characterization") to provide merit factors for texture and color measurements. The light may be white or colored light on a 3-10 mm spot to mimic human vision. Typically flat samples are used, but curved surfaces can be measured with a very thin beam such as 0.5 mm. Small samples as well as large products can be measured. In particular, by working with a camera that produces images of the entire hemisphere, the Parousiameter has been found to reduce the time needed to measure a surface's reflection compared other devices such as the moving-detector goniophotometer. Light beam 190 is a probe beam for translucence.

Figure 2:
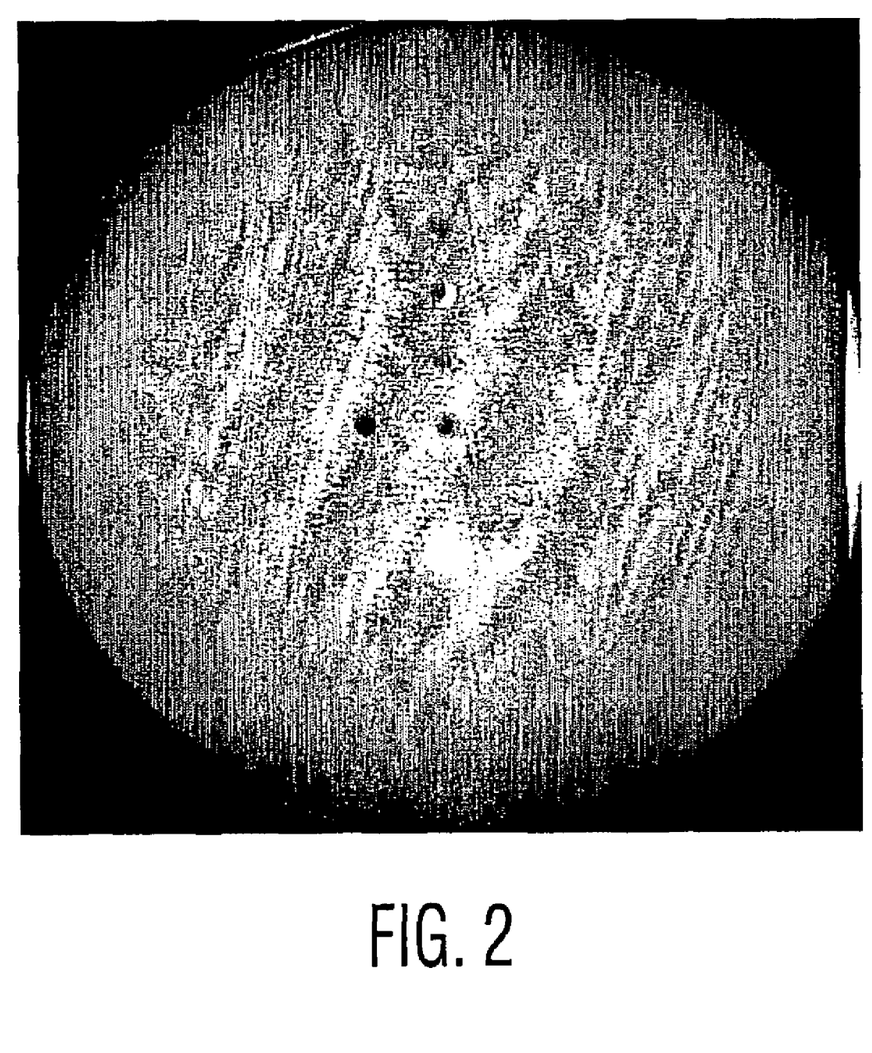
FIG. 2 illustrates an image of a test sample obtained using the scatterometer of FIG. 1.

However, the amount of data obtained by the Parousiameter can be extremely large. For example, a typical image (in this example made of a plastic product surface) that is obtained is shown in FIG. 2. The center of the image is the apex of the hemisphere, and the perimeter is the horizon. The dark spots are artifacts of the illumination and camera ports. Specifically, the leftmost dark spot is where the camera port is located, while the different spots arranged one after the other are ports through which the light beam is provided. The hemispherical dome is filled with diffuse light, bright in the middle and fainter towards the horizon, and there is a bright spot below the center that represents a direct surface reflection. Every point in the picture represents a different reflection angle and has a different intensity. The task is now to describe this intensity distribution in a tabular form. The typical image may easily contain a million data points lying on a regular grid, so that if all angles present are taken into account, an extremely large file is formed.

In particular, the data obtained by the camera is typically processed using a mathematical function such as the bi-directional reflection distribution function (BRDF) to produce the resulting image. This type of function describes the way that surfaces reflect and/or transmit light. For example, BRDFs are used in ray-tracing programs for the design of optical products such as lighting appendages, luminaries or optical systems such as lenses. However, as mentioned, the data necessary to define the BRDFs often results in extremely large files which cannot be processed quickly as required in manufacturing applications, for example.

A further problem with scatterometers, including the Parousiameter, is that image distortion of the hemispherical field of view can be significant.

Moreover, in the related field of deflectometric inspection, the deflectometric principle is very sensitive to small disturbances in smooth shapes such as automotive parts. On the other hand, if a large disturbance in the test sample is measured, the deformation of the reflected grid may become complicated and also out-of focus for the camera due to the optical power of concave forms. Therefore, a problem with such inspections is the limitation of the measuring dynamic range in deformations that can be measured.

The present invention addresses the above and other issues.

In one aspect, the invention provides a technique for reducing the amount of data necessary to define a scatterometric function that describes the intensity of light distribution of a target material at different points on a hemisphere, without loss of significant data.

In particular, a computer-implemented method for processing scatterometric data includes directing light toward a target material in a scatterometer, measuring an intensity of the light in the far field, after it is reflected from the target material, wherein the intensity is measured across a grid of points in a field of view provided on a screen of the scatterometer to obtain data representing the intensity across the field of view; determining variations in the intensity across the field of view, and defining at least one function describing the intensity of the light distribution tabular or in a mathematical way, across the field of view by varying a resolution with which the intensity data is used in different regions of the grid according to the determined variations in the intensity. Each of the different regions comprises at least one of the grid points.

In a further aspect of the invention, a technique is provided for reducing the image distortion of the hemispherical field of view in a scatterometer.

In particular, a scatterometer includes a light source for directing light toward a target material, a spherical screen for receiving the light after it is reflected from the target sample, and a convex spherical or aspherical mirror positioned to provide an image of the reflected light on the spherical screen to a camera.

In yet a further aspect of the invention, a technique is provided for increasing the dynamic range of measurement in an optical inspection system so that both small and large disturbances in a test sample can be accurately measured. The highly sensitive far field detection provided by deflectometry is extended with a near-field structured light facility that offers a large scale overview by addition of an extra lens group in the illumination light path.

In particular, an optical surface inspection apparatus includes a test surface, an illuminated patterned grid, an auxiliary lens provided between the test surface and the illuminated patterned grid for projecting the illuminated patterned grid on the test surface, and a camera focused on the illuminated patterned grid on the test surface as a real image to obtain at least a first image of the test surface.

In the drawings.

In all the Figures, corresponding parts are referenced by the same reference numerals.

I. Variable Density Grid for Scaterometric Functions with High Dynamic Range

As mentioned at the outset, imaging data that is obtained from a scatterometer such as the Parousiameter can form extremely large files that cannot be quickly processed as required in many applications such as manufacturing. For example, in such applications, a test sample may be periodically obtained from a production line to assess the quality of the manufactured products. A quick result must be obtained to avoid unnecessary delays on the production line. Moreover, increased data storage and processing requirements results in increased costs.

In particular, the function used to describe an image, such as the BRDF, has many coefficients or components that must accurately describe the salient features of the test sample over a wide dynamic range in which both small and large variations in the reflected or transmitted light intensity are experienced. In practice, intensity measurements are obtained in a grid of points in the hemispherical or other field of view. One possible solution is to lower the resolution of the function by using a coarser grid. However, this results in image blurring and the loss of critical information. For example, in the diffuse outer fields of the field of view, no sharp differences in intensity are present in many cases, i.e., there are no high spatial frequencies. Accordingly, it is no problem to reduce the resolution in those regions. However, when the reduced resolution is applied to regions of the field of view that have high spatial frequencies, e.g., due to rapid variations in the intensity, a problem results in that critical details can be lost. Specifically, in areas where there is no detail, this is not a problem, but around the specular reflection (or in parousiagrams of holograms that may be very complicated) the image gets blurred and critical information is lost. This makes it unacceptable to reduce the amount of data by making the grid coarser.

According to the invention, the composition of the grid is made dependent on the contents of the measurement. That is, the distance between grid points that are used in the function that describes the intensity across the field of view is made large in areas having no detail, and small near detailed regions. There are several possible ways to make the distance between the grid points variable. For example, the grid density can be made inversely proportional to the derivative of the intensity distribution. Thus, a higher grid density is used when there is a high variation in the intensity distribution, such as among neighboring points or regions of points in the grid. In another approach, a next data point can be placed at a location where the intensity has changed by a constant factor, e.g. 10% or a factor 2.5, or whatever value is convenient. A relative or absolute difference may be used. For example, if there is a sequence of (location, intensity value) pairs along a path in the field of view of, e.g., (x1, 10.0), (x2, 10.2), (x3, 10.4), (x4, 10.7), (x5, 10.9), (x6, 11.1), . . . , this can be reduced to (x1, 10.0), (x6, 11.1), . . . , using the 10% change criteria. The BRDF thus may contain data lines stating the position of a data point and its intensity, rather than assuming a fixed resolution grid. Essentially, the function describes the intensity of the light distribution by varying the resolution with which the intensity data is used in different regions/locations of the screen 130.

Figure 3:
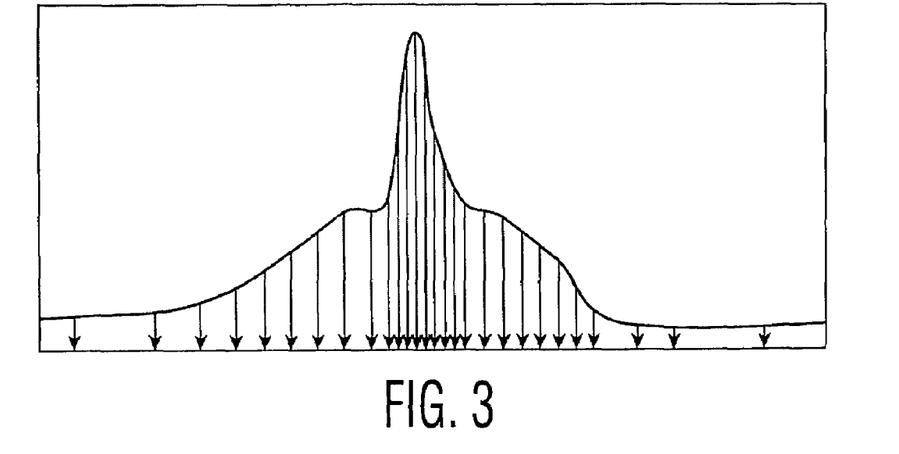
FIG. 3 illustrates a varying grid density based on intensity, according to the invention.

The general idea of a varying data grid is given in FIG. 3, which shows intensity vs. screen position. In particular, the curved graph is an intensity profile, and the vertical arrows point to imaginary positions of the variable grid. The varying spacing between the vertical arrows indicates a varying data resolution. The data compression depends on the contents of the data. It is estimated that a data compression of a factor of 100 can be easily achieved. Essentially, the resolution with which the intensity data is used in the different regions is varied between a maximum resolution and a minimum resolution so that an amount of data needed to define the function is reduced relative to a case where the function describes the intensity of the light distribution using only the maximum resolution.

Figure 4:
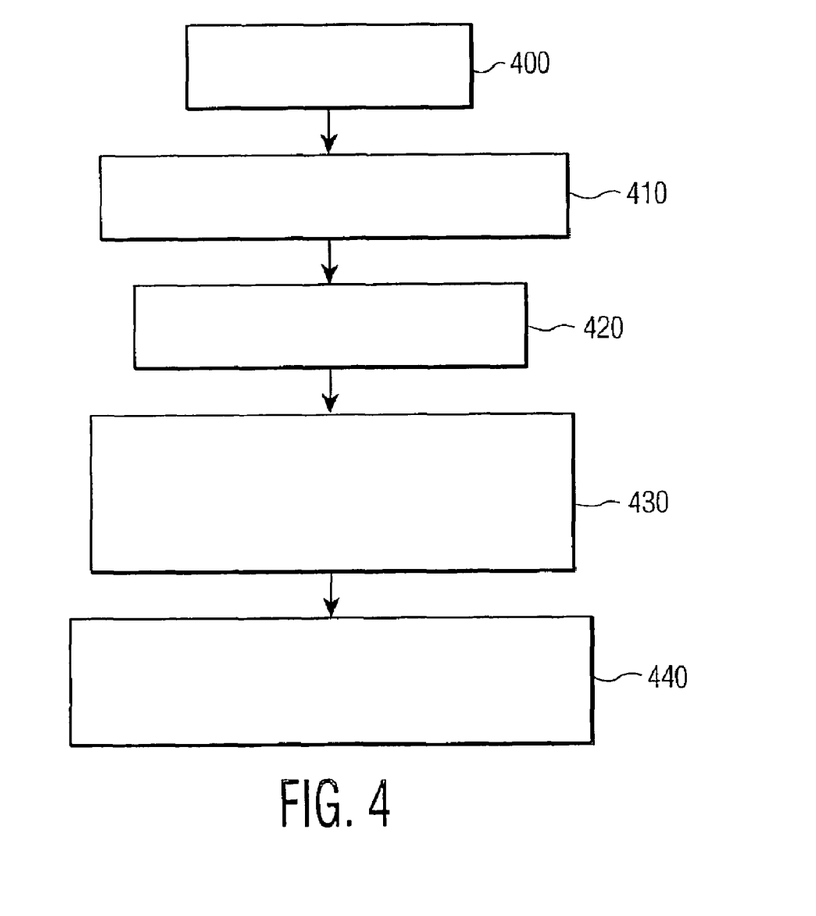
FIG. 4 illustrates a method for describing intensity variations in a field of view with compression, according to the invention.

FIG. 4 illustrates a method for describing intensity variations in a field of view with compression. Block 400 reads "direct light toward target material"; block 410 reads "measure intensity of reflected light at all grid points on screen"; block 420 reads "determine variations in the intensity distribution"; block 430 reads "determine varying resolutions for different regions of grid points based on the variations in the intensity distribution"; and block 440 reads "define a function describing the intensity distribution based on the varying resolutions".

At block 400, light is directed toward the target material. At block 410, the intensity of the reflected light distribution at all grid points on the screen of the scatterometer in the field of view is measured. At block 420, variations in the intensity distribution across the field of view are determined. This can be achieved, e.g., by looking at point-to-point variations, variations between every nth point, where n=1, 2, 3, ..., or by performing a spatial transform on the intensity data to determine a frequency with which the intensity data varies. At block 430, varying resolutions are determined for different regions of the grid based on the variations in the intensity distribution. The resolution, or density, indicates how many points in the region will be filtered out and not used in the function. A high resolution indicates no or few points will be filtered out. A low resolution indicates many points will be filtered out. Accordingly, a compression process is performed by allocating relatively less data to describe redundant grid points while allocating relatively more data to capture faster variations in the grid points. At block 440, using the varying resolutions, a function, such as the BRDF, is defined describing the intensity distribution across the different regions of the field of view.

The concept may be implemented in various applications, including ray tracing software, for example, to give the Parousiameter the capability to directly produce BRDFs readable in the ray tracing software. In such applications, without the data reduction technique described herein, a severe problem with file sizes can result. When the data-dependent flexibly variable grid is implemented, file sizes can be reduced by, for example, a factor 100, while still largely maintaining all relevant information. Other example areas of use include optical measurement, product design, functional optical product design, and CAD renderings for design applications but also for video games, films and other graphical uses.

Note that the Parousiameter is discussed as an example only, as the invention is suitable for use with other types of scatterometers and other types of optical measurement devices. Furthermore, while a hemispherical field of view was provided in an example, other shapes may be used. Moreover, the invention may be implemented on a general-purpose computer or other processing resource by providing a program storage device such as a memory, such as a hard disk or portable data storage media, for instance, that includes software instructions for execution by a processor to achieve the functionality described herein. A dedicated circuit as an ASIC may be used as well.

II. Aspherical Mirror for Improved Hemispheric Imaging

This aspect of the invention may be used in different applications, including imaging of hemispherical (or larger) fields of view, especially the screen of a parousiameter or other scatterometer. Referring again to FIG. 1, for imaging a hemispherical (180 degrees or more) field of view in a scatterometer, a wide-angle optical system such as a so-called fish-eye objective is needed, such as a lens or a mirror 170 which is typically located near the sample 180. However, the spherical mirror type such as a spherical convex mirror as used in all-sky cameras or in a conventional Parousiameter suffers from severe image distortion and astigmatism and coma to the edges of the field. All-sky cameras use special optical elements such as fish-eye lenses or spherical mirrors to acquire an image of the whole sky at once.

In particular, due to the a-centric (off center) placement of the mirror 170 and its spherical shape, an inevitable severe image distortion is formed. The image distortion is an instrumental constant and is. typical for the given geometrical layout of dome, mirror and camera. This image distortion can be measured using a calibrating hemispherical dome with markings at known positions, and in all following measuring images, corrected by software image processing in the computer.

Figure 5:
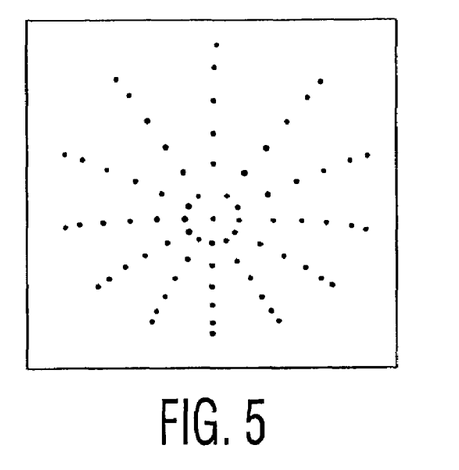
FIG. 5 illustrates a distorted parousiameter position calibration image.
Figure 6:
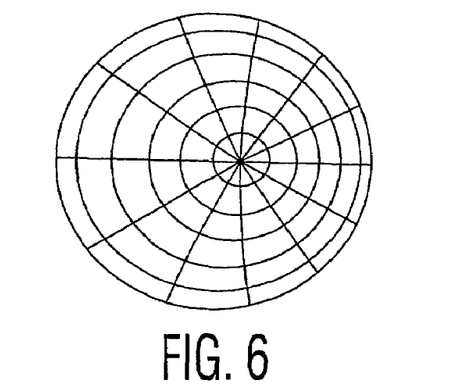
FIG. 6 illustrates the distorted image of FIG. 5, rotated 90 degrees counterclockwise and with 30 degree distant radii and 15 degree parallel circles added.

Image distortion correction is conventionally achieved in the following way. The typical Parousiameter position calibration image coming from the calibration measurement is given in FIG. 5. The image has been preprocessed to clearly bring out the markings on the dome. The faint circle at the perimeter is the 90°-horizon. This image is rotated and further processed to show the distorted grid with 30° distant radii and 15° distant parallel circles. FIG. 6 shows this distorted grid. As measurement reveals, there is a compression of latitude (height) degrees along the radius, caused by the spherical shape of the imaging mirror. This is a cosine effect, which is strongest along the edges of the image scale.

Figure 7:
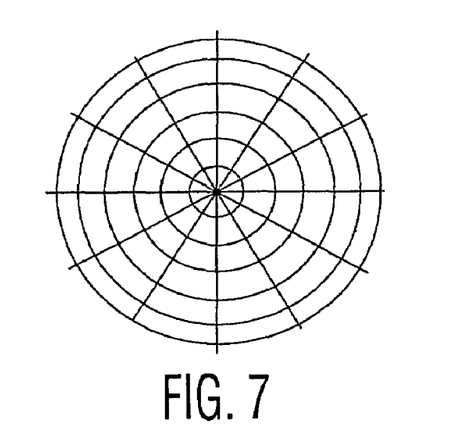
FIG. 7 illustrates the image of FIG. 6 after a software correction.

The clear sideways deformation is caused by the inherent a-centricity of the Parousiameter set-up. This effect would be smaller or even completely absent if the mirror was placed in the center of the hemisphere to be imaged, or the center of the dome screen, in the parousiameter case. However, the mirror and test sample 180 cannot be at the same location. All combined distortions cause the image scale, or magnification, to vary considerably (e.g., by a factor 2) over different regions of the image. This has consequences for image brightness distribution as well as for camera pixel scale. By further image processing (undistortion) the image must be brought to a stereographic projection as indicated in FIG. 7. However, during this process of correction, averaging errors occur that blur or perturb the image and cause loss of information. An undistortion method alternative to measured calibration for very nearly spherical dome shapes is using ab initio undistortion by recalculating all image elements back to the 'ideal' hemisphere and then re-projecting them onto the vantage point of the mirror.

According to the invention, it has been determined that the right choice of an aspherical profile reduces the image distortion so that the variation in image scale can be reduced. Hence a smaller (lossy) image processing correction is needed, thus reducing the overall loss of information. In particular, a part of the image distortion correction is shifted from software to hardware. Software image correction is lossy and takes time, whereas a hardware correction is loss-free and immediate. Image distortion and other aberrations can be influenced by the shape of the convex mirror. In most cases, the parousiameter imaging mirror is a full metal mirror that is manufactured by diamond turning on a high-precision lathe (surface roughness 1-3 nm) with programmable CNC trajectory control. The mirror is bare metal unprotected by 'enhancement coatings' made of hard layers of MgO or SiO2 because they have a wavelength dependence and hence would cause color shifts in the measurement. This makes it extremely easy to manufacture any shape of mirror simply by software programming. A further optical design freedom is in the location and angular adjustment of the mirror mount. By correcting part of the image distortion by hardware in this way, the residual necessary corrections by image processing in the computer are much smaller, so that fewer errors are introduced.

Figure 8:
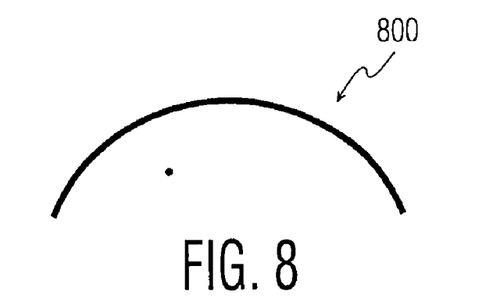
FIG. 8 illustrates a spherical mirror for use in a scatterometer.
Figure 9:
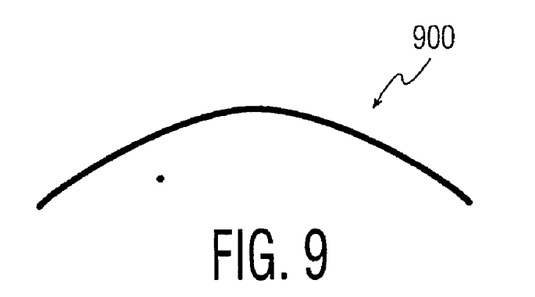
FIG. 9 illustrates an aspherical mirror for use in a scatterometer, according to the invention.
Figure 10:
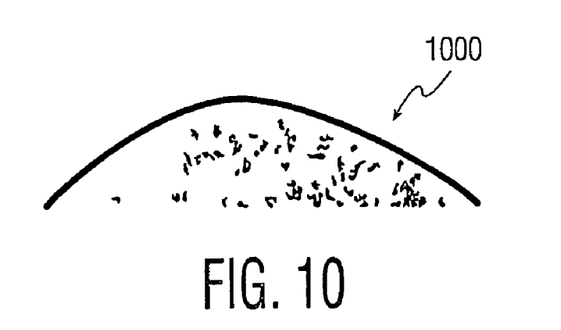
FIG. 10 illustrates a tilted aspherical mirror for use in a scatterometer, according to the invention.

FIG. 8 illustrates a spherical mirror 800 which results in significant distortion, while FIGS. 9 and 10 illustrate an aspherical mirror 900 and a tilted aspherical mirror 1000, respectively, which reduce distortion according to the invention. The mirror may be figured to shapes that generally have a larger radius of curvature towards their perimeters, as to magnify the image on its edges as compared to the behavior of a spherical shape. The optimum aspherical shape can be calculated exactly by ray tracing the whole optical system of the given configuration. This optimum shape can be approached by generic shapes, such as inverse cosines, conical sections or polynomials, or any other convenient shape. Furthermore, this mirror shape can be made a-centric and/or with a tilted axis as indicated in the qualitative example above, in the same or in a separate operation. It is possible to configure the mirror so that a fully undistorted image is formed but this option requires a complicated aspherical and asymmetric mirror form, that is relatively expensive to manufacture.

Figure 11:
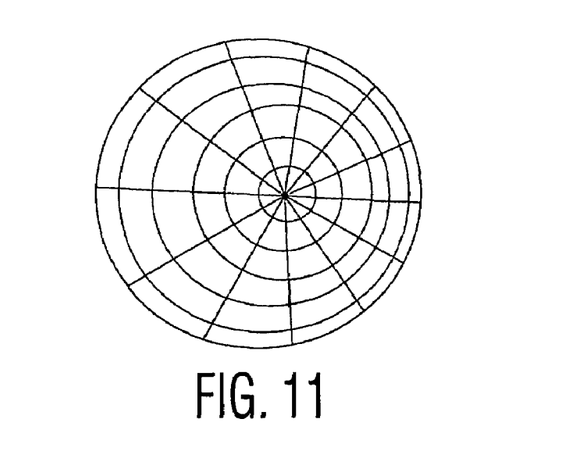
FIG. 11 illustrates a distorted image obtained using the spherical mirror of FIG. 8.
Figure 12:
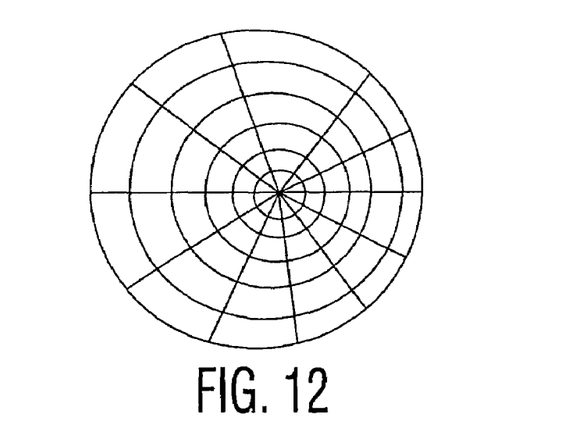
FIG. 12 illustrates an image obtained using the aspherical mirror of FIG. 9, according to the invention.
Figure 13:
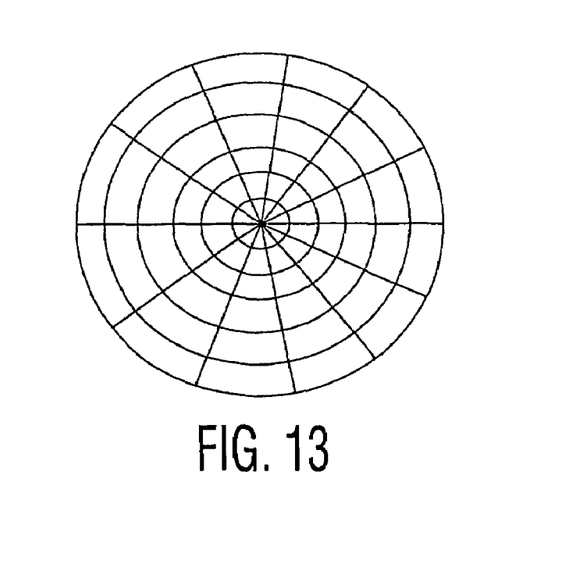
FIG. 13 illustrates an image obtained using the tilted aspherical mirror of FIG. 10, according to the invention.

FIG. 11 illustrates a deformed image grid using the spherical mirror of FIG. 8. FIGS. 12 and 13 are calculated examples of the effects of less deformed image grids, according to the invention. In particular, FIG. 12 illustrates an image corrected using the aspherical mirror of FIG. 9. FIG. 13 illustrates an image corrected using the tilted aspherical mirror of FIG. 10. As can be seen, the use of an aspherical mirror significantly reduces the distortion of imaging the screen of the scatterometer.

Figure 14:
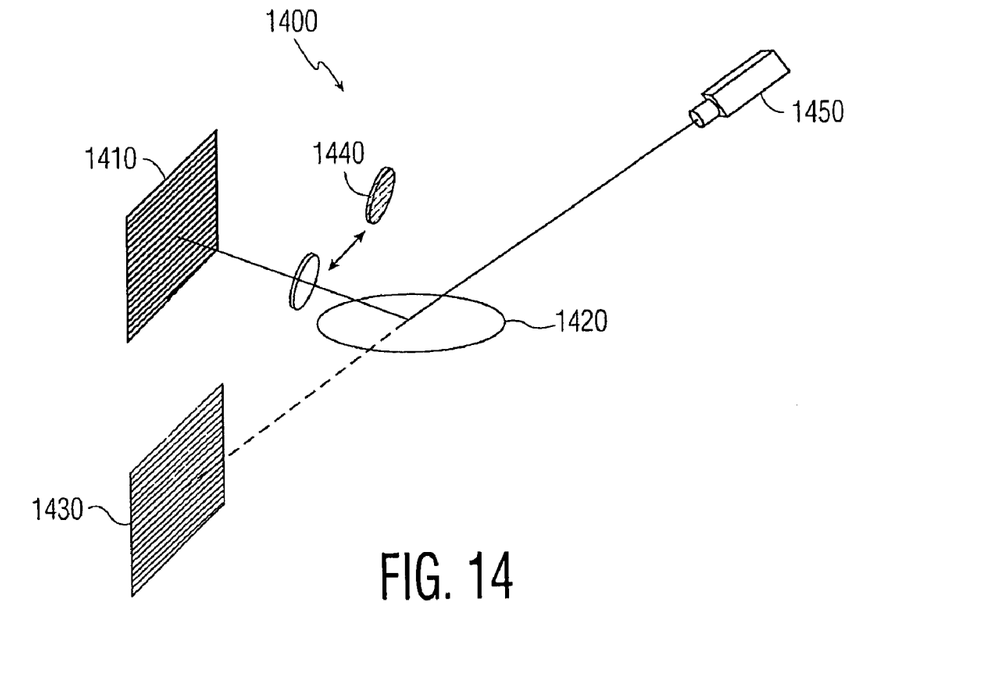
FIG. 14 illustrates an optical surface inspection apparatus configured as a deflectometer, where a camera is focused on a virtual image of a patterned grid.

III. Combined Far Field Deflectometer And Near Field Structured Light Profile Meter Optical surface inspection system (OSIS) are useful in various applications, such as automotive quality monitoring and repair, to assess the surface of a target material. In particular, the principle of deflectometry for finding flaws in a surface is well known. A setup using deflectometry is known as a 'deukometer'. FIG. 14 provides a setup for OSIS 1400 with an illuminated patterned grid reflecting in the test surface. In particular, a light source (not shown) illuminates a patterned grid 1410 so that an image of the grid is reflected by the test surface 1420 to provide a reflected image 1430 of the grid as a virtual image. An auxiliary lens 1440 is in an inactive position. A camera 1450 focuses on the virtual image 1430 to provide an image of the test surface 1420. However, with this approach, any deformations in the test surface 1420 strongly deform the reflection 1430 of the illuminated grid 1410. For example, an example of this deformation is given in FIG. 15, which shows a small dent in an automotive panel. It is clearly visible that the general shape of the panel is shown in large curvatures of the panel, while the small disturbances cause glitches in the contours.

As mentioned, the deflectometric principle is very sensitive for small disturbances in smooth shapes such as automotive parts. On the other hand, if a large disturbance in the test sample is measured, the deformation of the reflected grid may become complicated and out-of focus for the camera due to the optical power of concave forms. Therefore, a problem with deflectometry is the limitation of the measuring dynamic range.

Figure 16:
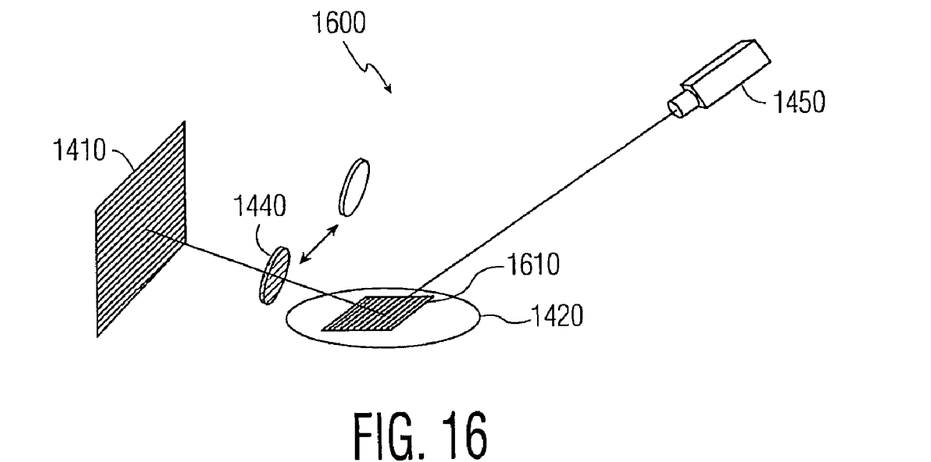
FIG. 16 illustrates an optical surface inspection apparatus configured for imaging by triangulation, where a camera is focused on a real image of a patterned grid, according to the invention.

In accordance with the invention, the modified OSIS 1600 of FIG. 16 provides an effective way to enlarge the measuring range. In particular, the apparatus 1400 is modified by bringing the virtual grid image 1430 to the test surface 1420, i.e., by projecting a real grid image 1610 on the surface 1420 instead of a virtual reflected image at infinity. This limits the sensitivity but enlarges the range. Advantageously, this modification can be achieved by using a simple extra lens group in the illumination path together with a refocus of the camera 1450. In particular, the addition to the original OSIS setup 1400 involves moving the auxiliary lens 1440 to an active position between the illuminated patterned grid 1410 and the test surface 1420 to project the illuminated patterned grid 1410 on the test surface 1420. If the lens 1440 is placed in the active position, the grid 1410 is imaged on the surface 1420 and the camera 1450 is refocused on the test surface. This refocusing can be done in the camera's lens and/or by the addition of a second auxiliary lens in the camera's light path. In the apparatus 1600, the curvature of the actual projected grid stripes on the surface 1420 is measured by triangulation. This method is less sensitive than the apparatus 1400, but results in a much larger range.

Figure 15:
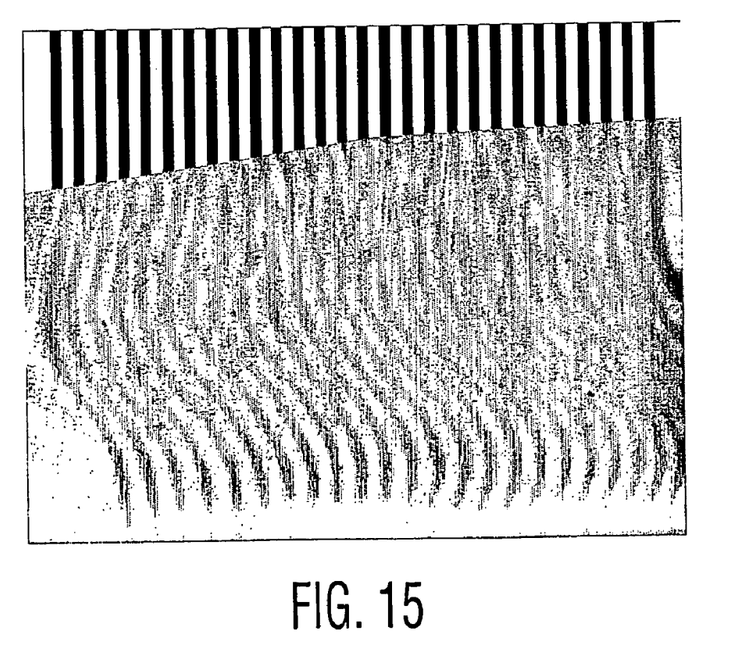
FIG. 15 illustrates an image of an automotive panel with a small dent obtained using the apparatus of FIG. 14.
Figure 17:
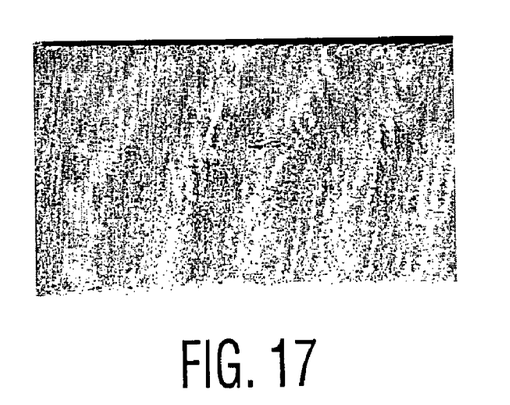
FIG. 17 illustrates an image of an automotive panel with a small dent obtained using the apparatus of FIG. 14.
Figure 18:
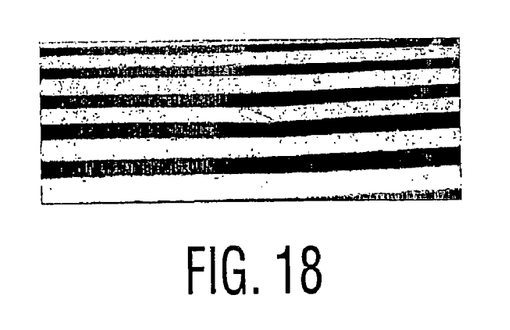
FIG. 18 illustrates an image of an automotive panel with a small dent obtained using the apparatus of FIG. 16, according to the invention.
Figure 19:
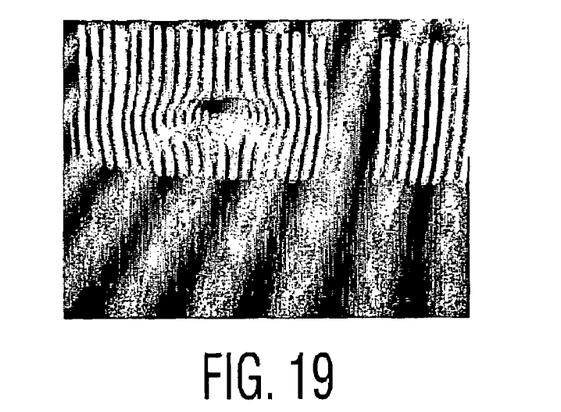
FIG. 19 illustrates a combined image of an automotive panel with a small dent obtained using the apparatus configured as in FIG. 14 and FIG. 16, according to the invention.

FIG. 17 is an image of the same small dent in an automotive panel as in FIG. 15 obtained using deflectometry according to the apparatus of FIG. 14. The dent is approximately 1 cm wide and 0.5 mm deep. FIG. 18 is a corresponding image obtained using triangulation according to the apparatus of FIG. 16, where the dent is more clearly seen. FIG. 19 is an image that combines the images obtained using the apparatus of FIG. 14 and FIG. 16. The data processing 112 function may perform the necessary processing to provide the combined image. Furthermore, an automated device may be used to move the lens 1440 between the inactive and active positions to obtain images by both techniques that can be combined. In the inactive position of FIG. 14, the lens 1440 is not active. In FIG. 19, the dark bands are the projected pattern with the contours running practically straight. The reflected grid, however, shows heavy deformations.

Figure 20:
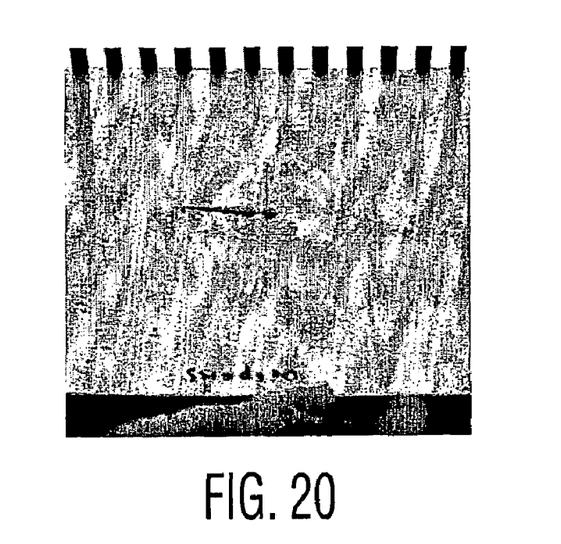
FIG. 20 illustrates an image of an automotive panel with a large dent obtained using the apparatus of FIG. 14.
Figure 21:
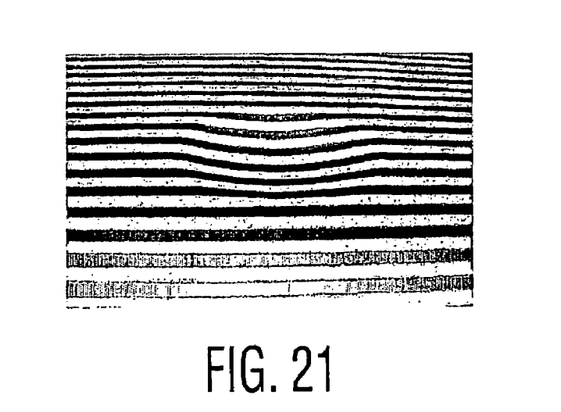
FIG. 21 illustrates an image of an automotive panel with a large dent obtained using the apparatus of FIG. 16, according to the invention.

Deeper dents would be difficult to profile using the purely deflectometric apparatus 1400 because deflectometric reflections tend to form closed loops or in some cases severely defocused images. By changing the geometry and the incidence angle of the setup, it is possible to lower the sensitivity so that deeper dents can be profiled but with the loss of the high sensitivity. For example, FIG. 20 and FIG. 21 are images of an automotive panel with a dent that is approximately 6 cm wide and 6 mm deep. FIG. 20 shows the deformation using the 'coarse' deflectometric apparatus 1400 with a virtual reflected image, while FIG. 21 shows the triangulation method of the same dent with a real image of a grid projected on the surface using the apparatus 1600.

While there has been shown and described what are considered to be preferred embodiments of the invention, it will, of course, be understood that various modifications and changes in form or detail could readily be made without departing from the spirit of the invention. It is therefore intended that the invention not be limited to the exact forms described and illustrated, but should be construed to cover all modifications that may fall within the scope of the appended claims.

The invention claimed is:

1. A computer-implemented method for processing scatterometric data, comprising:

directing light (140) toward a target material (180) in a scatterometer (100);

measuring an intensity of the light (120), after it is reflected from the target material, wherein the intensity is measured across a grid of points in a field of view provided on a screen (130) of the scatterometer to obtain data representing the intensity across the field of view;

determining variations in the intensity across the field of view; and defining at least one function describing the intensity of the light distribution across the field of view by varying a resolution with which the intensity data is used in different regions of the grid according to the determined variations in the intensity;
wherein each of the different regions comprises at least one of the grid points.

2. The method of claim 1, wherein:
the defining the at least one function comprises describing the intensity of the light distribution by varying the resolution with which the intensity data is used in the different regions so that a lower resolution is used for regions having a lower variation in the intensity.

3. The method of claim 1, wherein:
the defining the at least one function comprises describing the intensity of the light distribution by varying the resolution with which the intensity data is used in the different regions between a maximum resolution and a minimum resolution so that an amount of data needed to define the at least one function is reduced relative to a case where the at least one function describes the intensity of the light distribution using only the maximum resolution.

4. The method of claim 1, wherein:
the defining the at least one function comprises describing the intensity of the light distribution by varying the resolution with which the intensity data is used in the different regions so that the resolution used for each of the different regions is inversely proportional to a rate of change of the intensity therein.

5. The method of claim 1, wherein:
the defining the at least one function comprises describing the intensity of the light distribution along a path of the field of view by using a subset of the different points which are on the path and which exhibit a predetermined change in intensity, from one point to another along the path.

6. The method of claim 5, wherein:
the predetermined change in intensity comprises an absolute intensity difference.

7. The method of claim 5, wherein:
the predetermined change in intensity comprises a relative intensity difference.

8. The method of claim 1, wherein:
the at least one function comprises a bi-directional reflection distribution function.

9. The method of claim 1, wherein:
the field of view comprises a spherical field of view, that may be composed of two separate hemispheres.

10. The method of claim 1, wherein:
the field of view comprises a hemispherical field of view.

11. A program storage device comprising instructions for execution by a processor to perform a method for processing scatterometric data, wherein light (140) is directed toward a target material (180) in a scatterometer (100), the method comprising:
measuring an intensity of the light (120), after it is reflected from the target material, wherein the intensity is measured across a grid of points in a field of view provided on a screen (130) of the scatterometer to obtain data representing the intensity across the field of view;
determining variations in the intensity across the field of view; and
defining at least one function describing the intensity of the light distribution across the field of view by varying a resolution with which the intensity data is used in different regions of the grid according to the determined variations in the intensity;
wherein each of the different regions comprises at least one of the grid points.

12. A scatterometer, comprising:
a light source (145) for directing light (140) toward a target material (180);
a spherical screen (130) for receiving the light after it is reflected from the target sample; and
an aspherical mirror (170, 900, 1000) positioned to provide an image of the reflected light on the spherical screen to a camera (110).

13. The scatterometer of claims 12, wherein:
the aspherical mirror comprises a tilted aspherical mirror (1000).

14. The scatterometer of claim 12, wherein:
the spherical screen (130) comprises a hemispherical screen.

15. The scatterometer of claim 12, wherein:
the target material is centrally positioned in the scatterometer; and
the aspherical mirror is positioned a-centrically in the scatterometer, offset from the target material.

* * * * *